(12) United States Patent
Kazar

(10) Patent No.: US 11,636,950 B2
(45) Date of Patent: *Apr. 25, 2023

(54) SYSTEM FOR NON-INVASIVE EXAMINATION OF BLOOD ENVIRONMENT PARAMETERS

(71) Applicant: Digital Blood Corporation, Miami, FL (US)

(72) Inventor: Pavel Kazar, Hrušov (SK)

(73) Assignee: DIGITAL BLOOD CORPORATION, Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/737,334

(22) Filed: May 5, 2022

(65) Prior Publication Data
US 2022/0262521 A1 Aug. 18, 2022

Related U.S. Application Data

(63) Continuation of application No. 17/295,568, filed as application No. PCT/US2020/019953 on Feb. 26, 2020, now Pat. No. 11,328,821.

(60) Provisional application No. 62/810,927, filed on Feb. 26, 2019.

(51) Int. Cl.
| | |
|---|---|
| *A61B 5/01* | (2006.01) |
| *A61B 5/145* | (2006.01) |
| *G16H 50/20* | (2018.01) |
| *G16H 10/40* | (2018.01) |
| *A61B 5/00* | (2006.01) |

(52) U.S. Cl.
CPC .............. *G16H 50/20* (2018.01); *A61B 5/01* (2013.01); *A61B 5/14542* (2013.01); *A61B 5/14546* (2013.01); *A61B 5/7225* (2013.01); *A61B 5/7425* (2013.01); *G16H 10/40* (2018.01)

(58) Field of Classification Search
CPC ....... A61B 5/145; A61B 5/14542; A61B 5/01; A61B 5/00
USPC ........ 600/301, 309, 310, 311, 320, 328, 549
See application file for complete search history.

(56) References Cited

U.S. PATENT DOCUMENTS

| | | |
|---|---|---|
| 4,488,557 A | 12/1984 | Engel |
| 5,127,077 A | 6/1992 | Iyer et al. |
| 5,355,880 A | 10/1994 | Thomas et al. |

(Continued)

FOREIGN PATENT DOCUMENTS

| | | |
|---|---|---|
| CA | 2099400 | 1/1994 |
| WO | 8002795 | 12/1980 |

*Primary Examiner* — Navin Natnithithadha
(74) *Attorney, Agent, or Firm* — Mark C. Johnson; Johnson Dalal

(57) ABSTRACT

A system for non-invasive examination of a user's blood environment parameters that includes having a plurality of user-input sensors operably configured to measure a partial pressure of O2 and CO2 in a user's blood, a temperature of the user, and a hemoglobin content in the user's blood, an external electronic display unit, and a computing unit with a communication interface and communicatively coupled to the external electronic display unit and the least four user-input sensors, the computing unit operably configured to cause a user's blood environment parameters to display on the external electronic display unit through use of a mathematical software application resident thereon and employing a model of the user's internal environment based on a mathematical expression of an equation for hemoglobin buffer and utilizing the data from the user-input sensors.

6 Claims, 2 Drawing Sheets

(56) References Cited

U.S. PATENT DOCUMENTS

| | | |
|---|---|---|
| 5,978,691 A | 11/1999 | Mills |
| 7,842,012 B2 | 11/2010 | Ellis et al. |
| 8,527,023 B2 | 9/2013 | Hayoz et al. |
| 2007/0208515 A1 | 9/2007 | Rana et al. |
| 2010/0130842 A1 | 5/2010 | Hayoz et al. |

SYSTEM FOR NON-INVASIVE EXAMINATION OF BLOOD ENVIRONMENT PARAMETERS

CROSS-REFERENCE TO RELATED APPLICATION

This is a continuation application of pending U.S. application Ser. No. 17/295,568, which is a national stage filing of International PCT Application No. PCT/US20/19953, filed Feb. 26, 2020, which claims priority to U.S. Provisional Patent Application No. 62/810,927, filed Feb. 26, 2019, the entirety of which are incorporated by reference.

TECHNICAL FIELD

The invention relates to the medicinal examination of blood environment parameters of users (also referred to herein as "patients") and represents an appliance and method applicable in medical practice enabling noninvasive measuring of acidobasic and ionic equilibrium of blood environment and the parameters which are derived from them.

PRESENT STATE OF TECHNOLOGY

Present medical techniques of examination and continuous monitoring of the parameters of blood environment, especially some parameters of acidobasic and ionic equilibrium of blood gases and the parameters derived from them, are based on so-called "blood" methods measuring values of internal environment parameters, such as examination of acidobasic equilibrium of ions, on blood samples taken from patients.

In practice, such examination is carried out by means of various devices analyzing blood samples of examined patient. However, this blood sample has to be taken by invasive method. Analyzers in common use provide mostly a limited number of values of blood parameters. Noninvasive examination of blood environment parameters is not commonly used in medical practice although some analyzer designs for monitoring blood gases, analyzing the blood image or other parameters of blood internal environment are known from the patent literature.

Among the analyzers in common use employing so-called "blood" method it is for example the analyzer according to the U.S. Pat. No. 4,854,321 which describes an optical system for monitoring blood gases. The blood gases are monitored by unified probe containing several scoops for hemochrome and the immobilized hemochrome in these scoops whereby the hemochrome is exposed to the influence of blood gases. Optical fibers and waveguides connected to the hemochrome scoops enable the light to be guided from the light source as hemochrome and light, due to the absorption or spontaneous hemochrome emission, and to be returned back to the detector of light. Intensity, phase shift or other mechanism of returned light emission is a standard of partial pressure of respective blood gas. While applying this type of analyzer it is necessary to insert a probe into the bloodstream.

Another known solution of "blood" method is represented by the analyzer of blood image according to U.S. Pat. No. 7,826,978 describing the blood image analyzer containing a unit for capturing a blood image of the sample, an analyzing part for analysis of the sample on the basis of the blood image, an identification reader for reading the identification information from the sample which is assigned to the sample; a transportation part for transporting the sample to the identification information reader and an image capturing unit; a first detector for detecting the sample at a first detection position on a pathway of the sample transported by the transportation part; a display and a control unit for controlling the display, so as to display, based on a detection result by the first detector, a screen including a first identification information display region, wherein the first identification information display region displays identification information of the sample being at the first detection position. While applying this type of analyzer it is necessary to take a blood sample from a patient.

Disadvantages of present methods or techniques of examining the parameters of blood environment consist especially in the "blood" examination as such while the blood is taken from a patient's body. This may cause the distortion of measured values due to blood clotting or hemolysis, the blood samples can be contaminated by persons sampling the blood or the persons can be exposed to contamination by the patient's blood while they are taking samples.

Furthermore the present methods analyzing the parameters of internal environment which are dependent on taking patient's blood are questionable if they are applied to specific patients, namely to premature infants or patients with burn injury of high degree. In this case the blood sampling is virtually impossible.

Noninvasive solutions of the analysis of internal environment parameters use various cybernetic mathematical models. Cybernetics is a science dealing with general principles of controlling and transferring information in living organisms. It uses primarily mathematical models for the process description. Cybernetics is based on the knowledge that the processes in living organisms can be described by mathematical equations like the analogical processes in technical devices. The foundation of this approach was laid by Norbert Wiener, an American mathematician, who published the book "Cybernetics: Or Control and Communication in the Animals and the Machines" in the year 1948.

One of the known noninvasive solutions of measuring patient's blood internal environment is the solution according to SK patent SK288359 describing the application for determining parameters of blood internal environment. The device contains an electrode for scanning the partial pressure of oxygen, an electrode for scanning the pressure of carbon dioxide. These electrodes are connected through the measuring amplifier to the analytical and control complex with the output into the memory unit containing the database of patients. The analytical and control complex is connected to an image device, recorder and an additional advice for the access to the Internet. Furthermore the analytical and control complex is attached to the mixing device of breathing gases with the output of breathing gas and/or with the controlled dosing device with sets of infusion solutions. The appliance according to this invention allows measuring the internal blood environment on the basis of the transcutaneous electrode, while the results of acid base, i.e., the values of blood gases, are set with 90% accuracy and the values of ion balance are recalculated on the basis of the mathematical model of internal environment. However, these values, in particular for the specific cases of patients, can differ substantially from the real values obtained by the classical method with the necessary blood sampling and its subsequent processing by the chemical analyzer. This solution in particular does not allow the precise measurement if patients have elevated temperature at the moment or higher values of hemoglobin in blood, consequently if patients are in a critical state.

OVERVIEW OF TECHNICAL DRAWINGS

The appliance for noninvasive examination of blood environment parameters in accordance with the presented invention will be closer explained by means of drawings.

SUBJECT MATTER OF THE INVENTION

The object of the presented invention is an appliance, acidobasic analyzer, enabling fast, simple and maximum accurate examination of blood environment parameters, especially some parameters of acidobasic and ionic equilibrium of blood gases and the parameters derived from them which are carried out by noninvasive transcutaneous method.

Figure 1:
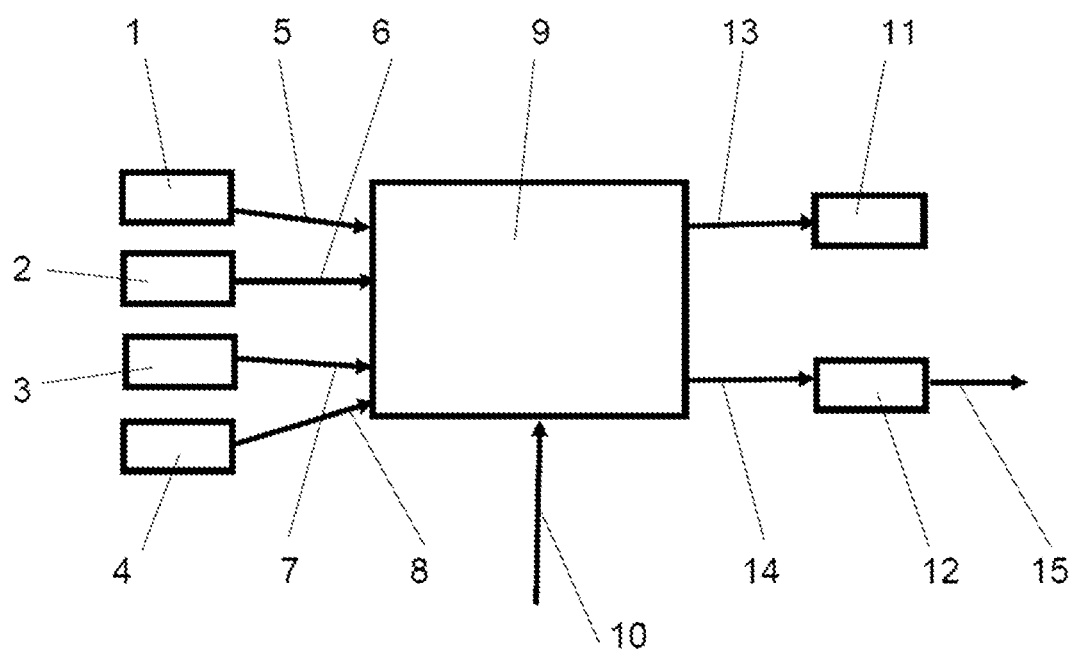
FIG. 1 represents a block diagram of connections of individual components of the appliance with the inputs of individual measured parameters and with the outputs into the displaying device, and other elements.
Figure 2:
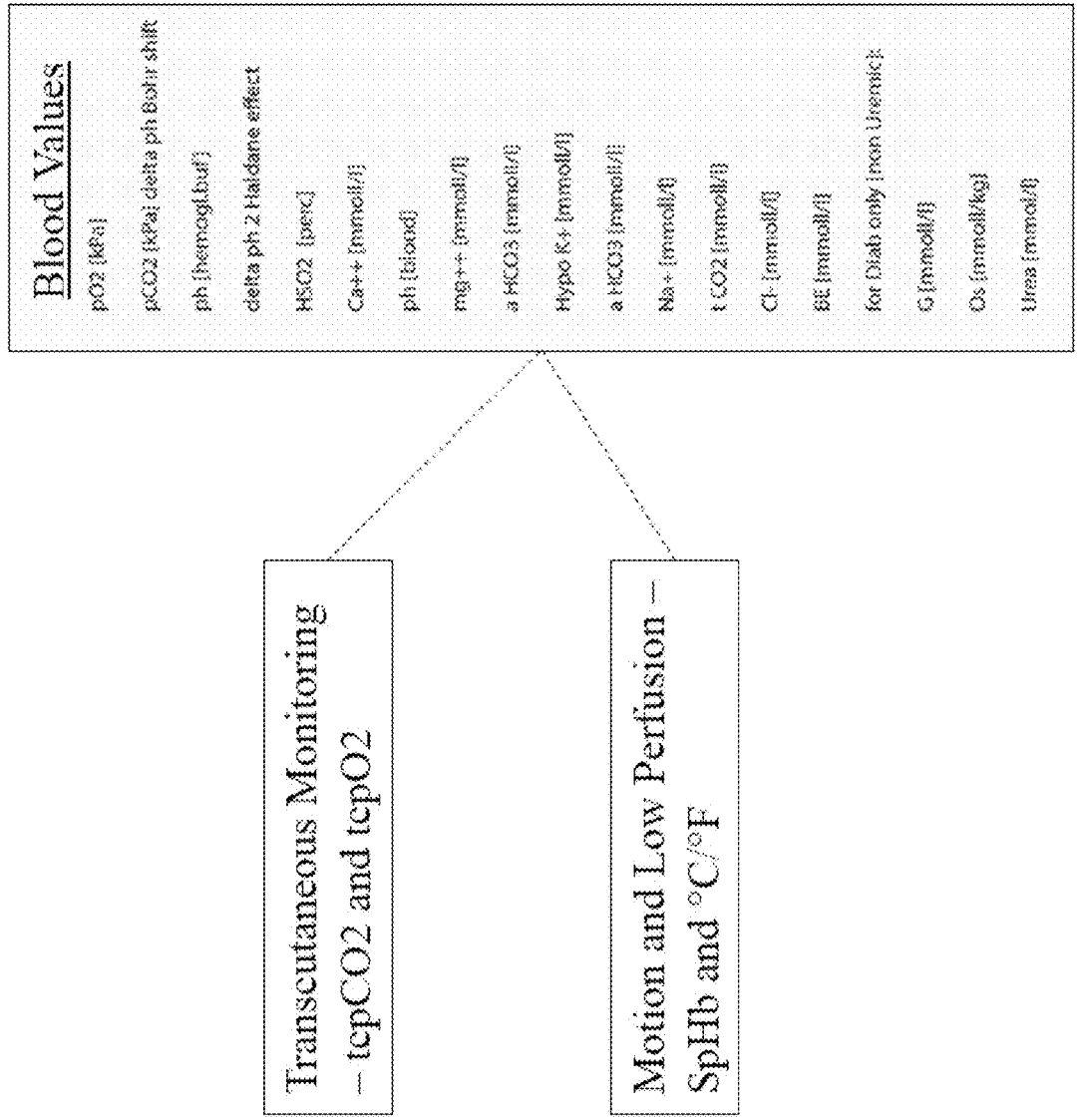
FIG. 2 represents both the scheme of 4 input characteristics of internal environment of a patient and the overview of 19 characteristics of internal environment of a patient which are obtained and displayed by the appliance for noninvasive examination of parameters of blood environment according one embodiment of the invention.

As depicted in FIGS. 1-2, the principle of the appliance for noninvasive examination of blood environment, containing input sensors, a computing unit block, an external displaying unit and a communication interface, is based on the fact that it comprises at least one sensor for measuring the partial pressure of O2 in patient's blood, a sensor of partial pressure of CO2 in patient's blood, a sensor of patient's temperature, and a sensor of hemoglobin contents in patient's blood which are connected through the analogue and/or digital inputs to the computing unit block which contains mathematical software operating with the model of patient's internal environment based on the mathematical expression of the equation for hemoglobin buffer, of the so-called Henderson-Hasselbach equation, used by means of the so-called Haldane Effect and simulating the processes which are involved in the so-called Bohr Effect.

Air and food are the fuel for constantly ongoing processes in the human body. The above-mentioned solution is based on the fact that our body uses two inputs that affect the whole of our internal system. The first entry is breathing when our lungs receive oxygen and produce blood gases, and the second input is eating which produces elements. This corresponds to two circuits, the respiratory and the gastroenterological circuits. The mathematical software operates with these circuits in this solution according to the invention.

The elements and blood gases are transferred by blood, there is constant communication between these two circuits and these circuits influence each other. In order to monitor this complex system safely and accurately, it is necessary to place four sensors on the patient's body, the sensor for measuring the partial pressure of O2 in the blood of a patient, the sensor of partial pressure of CO2 in the blood of a patient, the sensor of patient's temperature and the sensor of hemoglobin content in the blood of a patient which constantly monitor and take the values that are inputs of the block of processing units. These measured values are processed in real time by the mathematical software to be displayed on the external display unit or sent for further processing through the communication interface.

Measured values from the individual sensors are internally interconnected in the mathematical algorithms therefore each change of one measured input value that can change on each sensor independently, affects all the values displayed which provides the values of blood gases and measured elements (ions) with maximum accuracy.

In comparison with existing solutions, this advice for noninvasive examination of blood environment parameters was supplemented with two additional sensors, namely the sensor of patient's temperature and the sensor of hemoglobin content in blood of a patient. The influence of temperature on the blood environment is minimized in the current medical practice. However, it is apparent that the human body starts to defense itself even if the change of temperature is two tenths of a degree; the processes which are initiated are not still manifested externally and perceived by a patient nor the doctor can register any changes on a patient's state. Therefore any little change in temperature of human body has a substantial impact on the values of blood gases, as well as on the values of measured elements (ions) and their accuracy. Consequently, the values obtained from the temperature sensor of a patient have a decisive influence on the mathematical algorithms which compute additional values of blood gases and measured elements.

Until recently, the values of hemoglobin were impossible to gain by the noninvasive and continual manner. It was necessary to obtain them by the invasive method and the obtained results were only of an informative character and usually several hours old which made the exact calculation of values impossible. Today the hemoglobin sensors for noninvasive and continuous measurement are available. Owing to them, it is possible to achieve an absolute accuracy of measurement.

The complexity and variability of the blood internal environment can be demonstrated on the following examples. The optimal value of blood pH is within the range of 7.35-7.45. This range is very narrow but of a vital importance whereby the change of blood pH of 0.40, no matter if it is increased or decreased, can be decisive for patient's life. The above-mentioned range applies for 36.6° C. as which is a usual temperature of human body. At this temperature the value of hemoglobin is:

| | |
|---|---|
| Men | 135-170 |
| Women | 120-160 |
| Children | 120-180 |
| pO2 value | 9.9-14.4 |
| pCO2 value | 4.7-7 |

The change in temperature, or possibly in other input characteristics will influence the values of other characteristics and the consequent calculations.

In practice, owing to the included mathematical software operating with the model of patient's internal environment, 4 values are obtained from the sensor for measuring the partial pressure of O2 in patient's blood, from the sensor for partial pressure of CO2 in patient's blood, from the sensor of a patient's temperature and from the sensor of hemoglobin content in patient's blood. On the basis of these values additional 15 values characterizing the blood internal environment of a patient are determined. On the whole, this mathematical software measures or calculates 19 characteristics; each of them is variable and can reach different values, so the processed characteristics can be in thousand combinations. While designing the mathematical software, the experience acquired by measuring the blood by the classical invasive method was applied in the software, i.e., the method where standard chemical analyzers were used for the blood analysis of patients of different age groups from new-born children to dying patients. The evaluation of the characteristics of patient's internal blood environment is fully automatic.

The mentioned type of mathematical model of patient's internal environment, namely the respiratory and gastroenterology components, constitutes the basic feedback of cybernetics of patient's internal environment which enables to simulate the cybernetic processes of patient's internal environment by computer, if this block of computing unit is provided at least by an output to the external display unit or to the record unit and an output to the communication interface permitting the access to the Internet.

In case of the analogue input sensors, the block of computing unit digitalizes their analog signals simultaneously with the aid of included mathematical software. Then the mathematical software implements a suitable model of patient's internal environment from the models stored in the software of computing unit and computes the parameters of the blood internal environment of a patient. The access to the choice of a suitable model is given to the operator as well through the input to the block of computing unit. The person can choose a model of patient's internal environment which complies with a particular patient. The results calculated by the block of computing unit according to the chosen model of patient's internal environment can be displayed by the attached imaging component which can be connected both by standard wire transfer elements and by wireless connection. The equations characterizing the Haldane Effect, the Henderson-Hasselbach equations etc. are necessary for the calculation of blood gases of internal environment (acid base). These equations are transformed into algorithms which enable us to obtain real results of blood gases on the basis of the values from the sensors. These influence also the algorithms for the calculation of ion elements. Therefore it was necessary to complete the device with two additional sensors, a sensor measuring patient's temperature and a sensor for measuring hemoglobin content in patient's blood.

At the same time the exact quotient of respiratory and gastroenterological components in the model of internal environment of a patient determines a new parameter, the so-called shift in Haldane effect which is given at the value from 3 to 18 kPa or mmol of the partial pressure of CO2. The relations between the partial pressure of O2 and the saturation of HbO2 are given by the so-called Hill equation and by its equilibrium constant in the model of patient's internal environment. Other parameters of the model of internal environment of a patient, standard quantity of hydrogen carbonate and total O2 are determined by the modifications of the Henderson-Hasselbach equation with utilization of a new parameter "$\Delta ph_2$". Newly defined parameter "shift in the Haldane Effect" denoted as "$\Delta ph_2$" is a component of the equation for calculation of blood pH $$ph = 6.1 + \Delta ph1 + \Delta ph2$$

where pH=blood pH $\Delta ph1$=the Bohr Shift $\Delta ph2$=shift in the Haldane Effect whereby the Bohr effect or the shift in the Bohr effect is also a component of algorithm of the basic feedback of the relation of external environment—patient's lungs—cybernetics of patient's blood internal environment as the exactly organized biological system. The process of calculating the parameters and bonds is made in the block of computing unit containing mathematical software for determining the relation of acidobasic equilibrium and ionic equilibrium in patient's blood.

The relation of acidobasic equilibrium and ionic equilibrium of individual ions contained in patient's blood, namely Ca, Mg and K in relation to current values of patient's blood pH, constitutes the feedback in the model of internal environment of a patient. On the basis of this model it is possible to determine the values of Cl and Na, i.e., the elements which get into the blood circulation from the gastrointestinal tract, whereas these relations are modeled by the so-called gastroenterological model of blood internal environment of a patient. Other parameters of blood, such as sugar and urea contents and osmolality of blood are given by the modification of the formula $$\text{Osmolality} = 2Na + \text{urea} + \text{sugar/glycaemia/}$$

The appliance with the software stored in the computing unit block represents a new generation of analyzers utilizing the cybernetics for the technical presentation of human biological capability, including the description of patient's blood internal environment which enables at the same time to control automatically patient's treatment, e.g., at the infusion therapy or oxygen therapy etc.

The appliance based on this invention allows a fast, simple and maximum accurate examination of the parameters of blood environment, especially some parameters of acidobasic and ionic equilibrium of blood gases and the parameters derived from them, in the noninvasive way without any blood clotting impact or hemolysis.

The basic version of the appliance based on this invention monitors acid base and ions continually and in noninvasive way and consequently calculates and evaluates the biochemical parameters of blood internal environment of a patient, accordingly by applying this method it is possible to evaluate also all chemical elements contained in the blood of examined patient in real time.

Therefore, advantages of the presented solution lie in the noninvasive and continuous examination at a patient's bed. Parameter values of the blood internal environment are monitored by a doctor directly on the displaying device of the external computer and the doctor can, according to measured values, react and improve the patient's health condition immediately. Another advantage of this presented solution is the fact that examining persons are not in contact with patient's blood while carrying out the measurements, the results of measurement are not distorted and examining persons are not exposed to the contamination in case of patient's disease transmitted by blood.

EXAMPLE OF INVENTION EMBODIMENT

In one embodiment of the present invention, the sensor-based system for non-invasive examination of a user's blood environment parameters includes a plurality of user-input sensors operably configured to measure a partial pressure of O2 in a user's blood, a partial pressure of CO2 in the user's blood, a temperature of the user, and a hemoglobin content in the user's blood. The system also includes an electronic display unit and a computing unit communicatively coupled to the electronic display unit and the plurality of user-input sensors through at least one of plurality of analog and digital inputs, the computing unit operably configured to cause a user's blood environment parameters to display on the electronic display unit, the user's blood environment parameters includes acidobasic and ionic equilibrium of blood gases, or parameters derived from acidobasic and ionic equilibrium of blood gases. The computing unit includes a non-transitory memory including a mathematical software application and a processor operably configured to execute the mathematical software application, wherein the processor is further configured to calculate, through the use of the mathematical software application, the user's blood environment parameters by employing a model of the user's internal environment based on a mathematical expression of an equation for a hemoglobin buffer, or "Henderson-Hasselbach" equation, and utilizing the partial pressure of O2 in the user's blood and wherein the partial pressure of CO2 in the user's blood, the temperature of the user, and the hemoglobin content in the user's blood received from the plurality of user-input sensors.

In another embodiment, the system includes at least four user-input sensors consisting essentially of a first sensor operably configured to measure the partial pressure of O2 in the user's blood, a second sensor operably configured to measure the partial pressure of CO2 in the user's blood, a third sensor operably configured to measure the temperature of the user, and a fourth sensor operably configured to measure the hemoglobin content in the user's blood, wherein the partial pressure of CO2 in the user's blood, the temperature of the user, and the hemoglobin content in the user's blood are received from the at least four user-input sensors.

The appliance for noninvasive examination of blood environment parameters comprises sensor 1 for measuring the partial pressure of O2 in patient's blood, sensor 2 measuring the partial pressure of CO2 in patient's blood, sensor 3 taking a patient's temperature, and sensor 4 measuring hemoglobin contents in patient's blood, block 9 of computing unit which contains mathematical software operating with a model of patient's internal environment, analogue and/or digital inputs 5, 6, 7 and 8 for interconnection of at least four user-input sensors 1, 2, 3 and 4 to the block 9 of the computing unit 9 (e.g., one or more processor(s) with a local or remote non-transitory memory operably coupled thereto—said computing unit 9 also potentially including an electronic controller), with output 13 to the external electronic displaying unit 11 (e.g., mobile phone user interface or other electronic device interface) and/or to the recording unit (e.g., non-transitory memory) with output 14 to the communication interface 12, permitting the access to the Internet by output 15. Said another way, in one embodiment, a first sensor 1 is operably configured to measure a partial pressure of O2 in a user's blood, a second sensor 2 is operably configured to measure a partial pressure of CO2 in the user's blood, a third sensor 3 is operably configured to measure a temperature of the user, and a fourth sensor 4 is operably configured to measure a hemoglobin content in the user's blood. To effectuate the same, the computing unit 9 is communicatively coupled to the external electronic display unit 11 and the at least four user-input sensors 1, 2, 3, 4 through at least one of plurality of analog and digital inputs (5, 6, 7, 8). This communication may be effectuated through wired or wireless means as those of skill in the art can appreciate. The computing unit 9 is operably configured to cause a user's blood environment parameters to display on the external electronic display unit 11 through use of a mathematical software application resident thereon and employing a model of the user's internal environment based on a mathematical expression of an equation for hemoglobin buffer, or "Henderson-Hasselbach" equation, and utilizing the partial pressure of O2 in the user's blood, the partial pressure of CO2 in the user's blood, the temperature of the user, and the hemoglobin content in the user's blood received from the least four user-input sensors 1, 2, 3, 4 as further described and exemplified herein.

In medical practice, a patient's examination is carried out by sensor 1 measuring the partial pressure of O2 in blood, sensor 2 measuring the partial pressure of CO2 in blood, sensor 3 taking temperature and sensor 4 measuring hemoglobin content in blood. The sensors are placed on patient's skin according to the recommendation of the sensor producer. For example the sensor measuring the hemoglobin content can be in the form of a clip which can be fixed on a well perfused part of human body, e.g., on a finger. The impulses of measured values are transferred into the data recognizer and after the signal is conditioned into a mathematical form, it is further transferred into block 9 of the computing unit to be processed where after the mathematical algorithms process them, these inputs 1, 2, 3 and 4 determine the current values of the cybernetics of internal environment of individual patients.

After the analysis is processed in the block 9 of the computing unit, the cybernetic parameters of internal environment are continuously displayed on the displaying unit of external PC in the form of acidobasic equilibrium, ionic equilibrium, osmolality etc. So an attending physician can monitor continuously dynamics of pathological process, improvement or deterioration of patient's health.

On the basis of electronic analysis which is carried out by the appliance for noninvasive examination of blood environment parameters according to this invention, it is possible to evaluate the following individual required parameters of acid base and parameters of elements in patient's blood, i.e. blood pH, current HCO-3, standard HCO-3, total CO2, values of the base excess, saturation of oxygen, as well as values of partial pressure of oxygen and carbon dioxide. At the same time the appliance according to the invention newly analyses from the measured parameters the levels of sodium, potassium, chlorides, ionized magnesium, ionized calcium as well as the levels of blood sugar, urea and the level of osmolality, hydration and other parameters of blood internal environment of a patient.

For example, the content of magnesium, Mg, in a user's blood environment is calculable by using the following relation:

$$Mg = CO_1 - (CO_2 \times (CO_3 - pH)),$$

wherein $CO_1$, $CO_2$, and $CO_3$ are exemplary coefficient values.

Note that the coefficient, $CO_1$, for the magnesium, Mg, is derived from temperature inputs received from the user, the coefficient, $CO_2$, is derived from standard accepted pH ranges (identified above), and the coefficient, $CO_3$, is derived from median pH values. In another example, the content of calcium, Ca, is calculable by using the following relation:

$$Ca = (Mg + CO_1)/CO_2,$$

wherein $CO_1$ and $CO_2$ are exemplary coefficient values.

Note that the coefficient, $CO_1$, for the calcium, Ca, is derived from pH in the user's blood and $CO_2$ is derived from hemoglobin. Accordingly, the appliance for noninvasive examination of blood environment parameters based on this invention enables to monitor continuously pO2 and pCO2 from patient's surface, his temperature and content of hemoglobin in his blood and to computerize subsequently the evaluation of other parameters with presenting the results on the monitor of external PC.

The appliance uses the mathematical software stored in the block of computing unit operating with the model of patient's internal environment based on the mathematical expression of the equation for hemoglobin buffer, of the so-called Henderson-Hasselbach equation, used by means of the so-called Haldane Effect and simulating the processes which are involved in the so-called Bohr Effect whereby the exact quotient of respiratory and gastroenterological components in the model of internal environment of a patient determines a new parameter, so-called shift in the Haldane Effect, given at certain value of partial pressure of CO2. In the model of patient's internal environment, the relations between the partial pressure of O2 and the saturation of HbO2 are given by the so-called Hill equation and by its equilibrium constant. Other parameters of the model of internal patient's environment, standard quantity of hydrogen carbonate and total O2 are determined by the modifications of the "Henderson-Hasselbach" equation with utilization of a new parameter "$\Delta ph_2$". The newly defined parameter "shift in the Haldane Effect" denoted as "$\Delta ph2$" is a component of the equation for calculation of blood pH $$ph = 6.1 + \Delta ph1 + \Delta ph2$$

where pH=blood pH
$\Delta ph1$=the Bohr shift
$\Delta ph2$=shift in the Haldane Effect
whereby the Bohr Effect or the shift in the Bohr Effect are also incorporated in the algorithm operating with the model of patient's blood internal environment as the exactly organized biological system. The process of calculating the parameters and bonds is made in the block of computing unit containing the software of this acidobasic ionic analyzer.

The relation of acidobasic equilibrium and ionic equilibrium of individual ions contained in patient's blood, namely Ca, Mg and K in relation to current values of patient's blood pH constitutes another feedback in the model of patient's internal environment. On the basis of this model it is possible to determine the values of Cl and Na whereas these relations are modeled by the so-called gastroenterological model of blood internal environment of a patient. Other parameters of blood, such as sugar and urea contents and osmolality of blood are given by the modification of the formula $$\text{Osmolality} = 2Na + \text{urea} + \text{sugar/glycaemia}/$$

Accordingly, the appliance, system, assembly, and method for noninvasive examination of blood environment parameters based on the presented invention enables to monitor pO2 and pCO2 continuously from the patient's surface, his temperature and content of hemoglobin in his blood as well as to computerize subsequently the evaluation of other parameters with presenting the results on the monitor of external PC in the form of acidobasic equilibrium, ionic equilibrium, osmolality etc. So an attending physician can monitor continuously dynamics of pathological process, improvement or deterioration of patient's health.

The possibility of noninvasive monitoring the blood gases and the parameters derived from them is of great benefit, e.g. for the departments of intensive care, because immediately after the measuring is carried out, the results of measured parameters are provided by the device which enables a physician to react promptly and thereby all possible complications during the treatment and the length of inpatients' stay at intensive care units can be reduced. It is beyond question that this technology will bring economic benefits to hospitals.

The appliance for noninvasive examination of blood environment parameters according to the presented invention can be extended by other devices or systems, such as the electromagnetic dosing system for dosing some missing substances or remedies to a patient.

INDUSTRIAL APPLICABILITY

The application for noninvasive examination of blood environment parameters according to the presented invention is serviceable in majority of hospital departments, especially in the intensive care units, in anesthesiology and in intensive care medicine as well as in doctors' consulting rooms.

What is claimed is:

1. A sensor-based system for non-invasive examination of a user's blood environment parameters comprising:
    a plurality of user-input sensors operably configured to measure:
        a partial pressure of O2 in a user's blood;
        a partial pressure of CO2 in the user's blood;
        a temperature of the user; and
        a hemoglobin content in the user's blood;
    an electronic display unit; and
    a computing unit communicatively coupled to the electronic display unit and the plurality of user-input sensors through at least one of plurality of analog and digital inputs, the computing unit operably configured to cause a user's blood environment parameters to display on the electronic display unit, the user's blood environment parameters includes acidobasic and ionic equilibrium of blood gases, or parameters derived from acidobasic and ionic equilibrium of blood gases, the computing unit comprising:
        a non-transitory memory including a mathematical software application, and
        a processor operably configured to execute the mathematical software application, the processor further configured to calculate, through the use of-the mathematical software application, the user's blood environment parameters by employing a model of the user's internal environment based on a mathematical expression of an equation for a hemoglobin buffer, or "Henderson-Hasselbach" equation, and utilizing the partial pressure of O2 in the user's blood, the partial pressure of CO2 in the user's blood, the temperature of the user, and the hemoglobin content in the user's blood received from the plurality of user-input sensors.

2. The system for non-invasive examination of a user's blood environment parameters according to claim 1, further comprising:
    at least four user-input sensors consisting essentially of a first sensor operably configured to measure the partial pressure of O2 in the user's blood, a second sensor operably configured to measure the partial pressure of CO2 in the user's blood, a third sensor operably configured to measure the temperature of the user, and a fourth sensor operably configured to measure the hemoglobin content in the user's blood, wherein the partial pressure of CO2 in the user's blood, the temperature of the user, and the hemoglobin content in the user's blood are received from the at least four user-input sensors.

3. The system for non-invasive examination of a user's blood environment parameters according to claim 2, further comprising:
   the at least four user-input sensors consisting essentially of the first sensor operably configured, using a transcutaneous electrode with the first sensor, to measure the partial pressure of O2 in the user's blood and the second sensor operably configured, using a transcutaneous electrode with the second sensor, to measure the partial pressure of CO2 in the user's blood.

4. The system for non-invasive examination of a user's blood environment parameters according to claim 1, wherein:
   the computing unit includes an output into the electronic display unit or into a recording unit and an output into a communication interface on the computing unit permitting both direct and remote access to the Internet.

5. The system for non-invasive examination of a user's blood environment parameters according to claim 1, wherein:
   the mathematical model of the user's internal environment serves as the basis for a determination of Chlorine and Sodium values, wherein the determination of Chlorine and Sodium values are mathematically modeled by a gastroenterological model of blood internal environment of a patient.

6. The system for non-invasive examination of a user's blood environment parameters according to claim 1, wherein:
   the mathematical model of user's internal environment serves as the basis for the determination of other parameters of the user's blood, including sugar, urea contents, and blood osmolality, which is provided by the following formula:

$$\text{Osmolality} = 2\text{Na} + \text{urea} + \text{sugar/glycaemia}/.$$

* * * * *